United States Patent [19]

Wolstrup et al.

[11] Patent Number: 5,643,568
[45] Date of Patent: Jul. 1, 1997

[54] SELECTION AND ISOLATION OF MICROFUNGI FOR USE IN BIOLOGICAL CONTROL OF PARASITIC NEMATODES IN ANIMALS

[76] Inventors: Jens Wolstrup, Amalievej 4A, Frederiksberg C, Denmark, DK-1875; Jørn Grønvold, Lundtoftegade 88, 2.tv., Copenhagen N, Denmark, DK-2200; Peter Nansen, Elmekrogen 2, Værløse, Denmark, DK-3500; Svend Aage Henriksen, Borrisveg 22, DK-2650 Hvidovre; Michael Larsen, Harsdorffsvej 1B, 2.tv., DK-1874 Frederiksberg C, both of Denmark

[21] Appl. No.: 204,345

[22] PCT Filed: Sep. 8, 1992

[86] PCT No.: PCT/DK92/00269

§ 371 Date: Jun. 20, 1994

§ 102(e) Date: Jun. 20, 1994

[87] PCT Pub. No.: WO93/05143

PCT Pub. Date: Mar. 18, 1993

[30] Foreign Application Priority Data

Sep. 9, 1991 [DK] Denmark ................................. 1582/91
Dec. 19, 1991 [DK] Denmark ................................. 2034/91

[51] Int. Cl.⁶ ........................ A01N 63/00; A01N 63/04; A01N 65/00; C12N 1/14
[52] U.S. Cl. ........................ 424/93.5; 435/234.1; 435/911; 426/2; 426/807
[58] Field of Search ................... 426/2, 807; 435/254.1, 435/911; 424/93.5

[56] References Cited

U.S. PATENT DOCUMENTS 4,689,231 8/1987 Zuckerman et al. ............... 424/195.1
5,051,255 9/1991 Devidas et al. ..................... 424/195.1

OTHER PUBLICATIONS

*ATCC Catalogue of Filamentous Fungi*, 18th ed., 1991, ed. S. C. Jong et al., p. 161.
Cooke, R.C. "Trans. Br. Mycol. Soc." vol. 53, #2, 1969, pp. 315–319.
Waller, P. J. "Parasitology Today." vol. 9, #11, 1993, pp. 429–431.
Grønvold, J. et al., "Veterinary Parasitology." vol. 48, 1993, pp. 311–325.
Waller, P. J. et al., "Int J. for Parasitology." vol. 23, #4, 1993, pp. 539–546.
Larsen, M. et al, "Veterinary Parasitology." vol. 53, #3/4, 1994, pp. 275–281.
Grønvold, J. et al, "Parasitololgy Today." vol. 9, #4, 1993, pp. 137–140.
Virad, M., "Revuew de Mycologie." vol. 41, 1977, pp. 415–426. (Original Plus Translation).
Larsen, M. et al., *J Helminthol (England)*, Sep. 1991, 65(3) pp. 193–200.
Gronvold, J. et al., *J Helminthol*, Jun. 1989, 63(2) pp. 115–126.
Nansen, P. et al., *Vet Parasitaol*, Jan. 1988, 26 (3–4) pp. 329–337.
Gronvold, J. et al., *J. Helminthol*, Jun. 1985, 59 (2) pp. 119–125.
Peloille, M., *IOBC/WPRS Bulletin*, International Union of Biological Sciences, 1991/XIV/2.

*Primary Examiner*—Irene Marx
*Assistant Examiner*—Kristin K. Larson
*Attorney, Agent, or Firm*—Darby & Darby

[57] ABSTRACT

In a process for the selection and isolation of predacious fungi for use in the biological control of parasitic nematodes in animals, compost and soil samples are subjected to a multi-step process consisting of 1) a primary stress selection step done in vitro; 2) a secondary stress selection step done in vivo, wherein the fungi which survived the in vitro stress selection step, are selected on the basis of their ability to pass through living animals and 3) isolation of the predacious fungi passing both selection steps and exhibiting a predacious capacity of at least 50% by dung pat assay. These fungi can than be subject to an optional field test experiment. The selected predacious fungi can be administered to the animals as a feed additive or in the form of a device, such as a lick stone or bolus. The selected fungi can also be used in a composition for veterinary treatment.

24 Claims, 3 Drawing Sheets

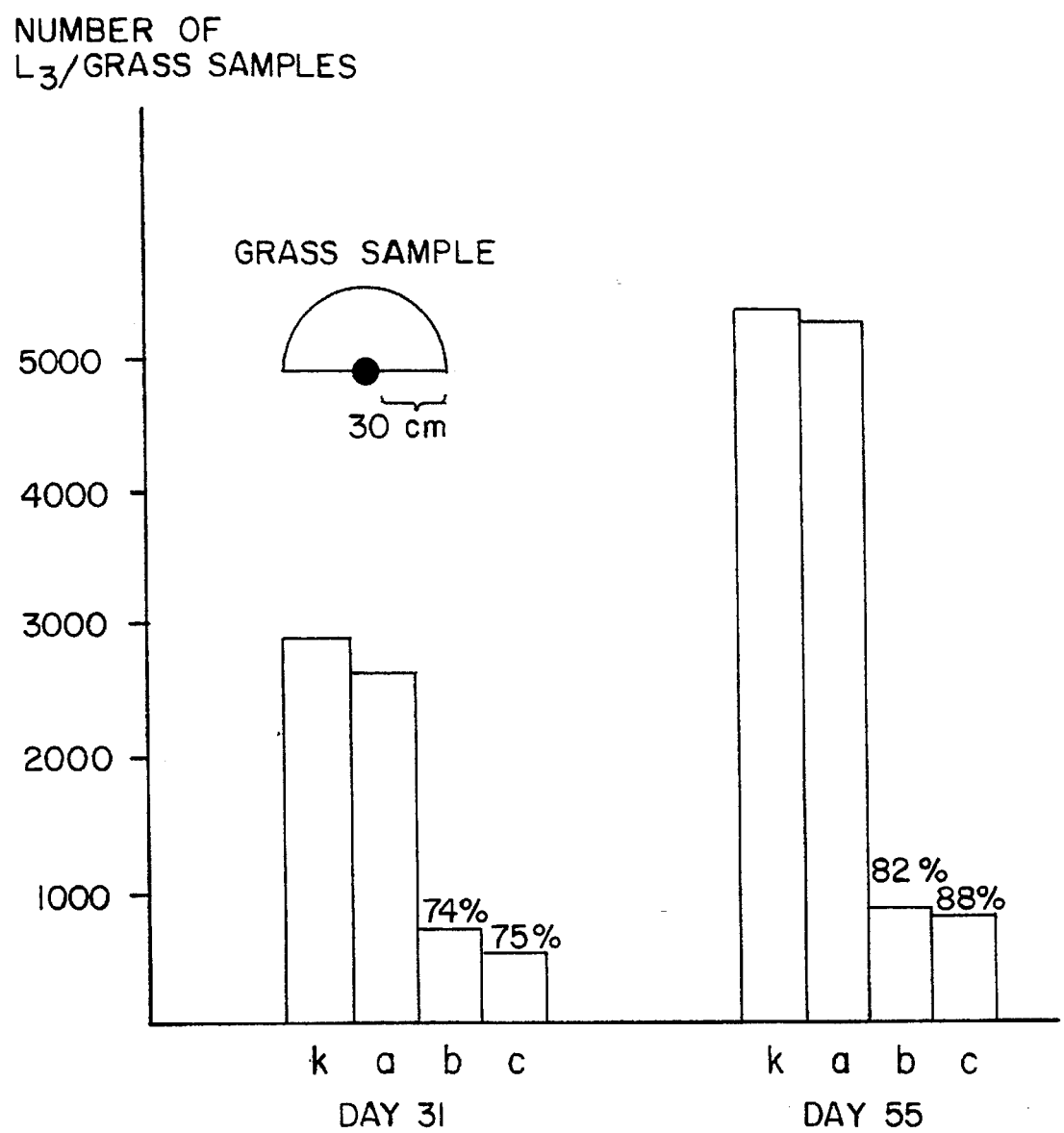

SELECTION AND ISOLATION OF MICROFUNGI FOR USE IN BIOLOGICAL CONTROL OF PARASITIC NEMATODES IN ANIMALS

This application was filed under 35 USA 371 as the national phase of PCT/DK92100269.

FIELD OF THE INVENTION

The present invention relates to a process for selection and isolation of nematophagous fungi to be used as biological control agents against infective larvae of parasitic nematodes such as *Ostertagia ostertagi* and *Cooperia oncophora* (Trichostrongylidae).

BACKGROUND OF THE INVENTION

Young calves which are put to pasture for the first time are susceptible to a large number of germs, i.e. threadlike small parasitic nematodes (Trichostrongylidae), which are parasites in the abomasum and intestine of cattle. These infections can cause serious diseases, such as diarrhea, indigestion, loss of weight, and death. But it is in particular the relatively mild infections which are of economic importance, since they are very widespread and result in poor growth, in particular at the end of the season.

Infected calves secrete the very small eggs of the nematodes in their faeces. FIG. 1 shows the life cycle of cattle nematode parasites. The mature parasites multiply by laying eggs in the intestinal tract of the cattle. The eggs have a size of 0.05–0.1 mm and are thin shelled. They are excreted with the dung of the animals. The larvae develop from the eggs in the cow pats on the pasture. The larvae go through three larval stages ($L_1$, $L_2$ and $L_3$). The third larval stage ($L_3$), which is infective, retain the cuticle of the second larval stage ($L_2$) as a protective sheath until they enter their host. In the cow pat, temperature, moisture, oxygen pressure and the natural enemies of the parasites are decisive for the number of eggs that develop to the infective stage. The infective larvae, having a length of up to 1 mm, are spread from the cow pat to the surrounding grass, in particular in connection with rainy weather. Most of the larvae are present within 30 cm from the rim of the cow pats. On the grass they may be eaten by grazing animals, and then they can continue their development in the intestinal tract of the animals up to maturity.

The parasitic development starts when $L_3$ larvae are ingested by cattle. $L_3$ exsheath in the rumen. A few days after the infection, exsheathed $L_3$ enter the abomasal glands, where they differentiate and increase in size. Three stages occur ($L_3$, $L_4$ and $L_5$), separated by two moults. Immature adult parasites ($L_5$) emerge from the glands around 18 days after the infection. During the next few days, they become sexually mature on the surface of the abomasal mucosa, resulting in excretion of eggs.

Since nematode parasites often cause great losses to farmers, it is very much of interest to control these parasites. Traditionally, this takes place by medical treatment, but farmers also try in various ways to protect grazing animals against eating large amount of larvae, e.g. by reducing the density of animals on the pasture so that they are not forced to graze the highly infected areas close to their own excrements. Animals can also be moved to a clean or low-infected field at the end of the summer when the danger of infection usually increases strongly.

However, these measures have a number of economic and practical drawbacks, making it desirable to find alternative methods of control. Thus, for a number of years efforts have been devoted to the development of methods for biological control of larvae of nematodes in cow pats already before they are spread as infective larvae to the grass. Biological control comprises the use of natural enemies of the nematodes, which are nematophagous fungi, also called predacious fungi, in this case.

Predacious fungi are microfungi which do not develop fruiting bodies, as is known from e.g. mushrooms, but have a growth form resembling mold. Predacious fungi are special having developed organs that are able to capture and kill small nematodes, including infective larvae of nematodes. Predacious fungi are originally terricolous fungi, but it has been found that they can also grow in cow pats. It is precisely here their beneficial effect should be used to kill large numbers of the infective larvae of parasitic intestinal worms.

FIG. 2 shows a nematode larva captured by a predatory fungus. The larva is captured in a sticky net consisting of three strong arcs. Where there is contact, the parasite is penetrated. Fungal hyphae extend from here to grow out and fill the body of the nematode which is eventually killed. Then the inner organs are dissolved and absorbed. The fungal mycelium inside the parasite is shown by dotted lines.

To utilize predacious fungi in practice it is necessary to select fungal species which can pass through the intestinal tract of cattle alive. Moreover, methods should be developed to produce large amounts of fungal material. It will hereby be possible to place predatory fungi in cow pats in the period during the grazing season when many parasite nematode larvae develop in cow pats.

So far all attempts to isolate efficient fungi which are able to pass the intestinal tract of animals, and thereby usable in biological control, have failed. It has also not been possible by any means to coat the fungal material in order to protect said material against exposure to the enzymes in the intestinal tract.

Since the discovery of nematophagous fungi about one hundred years ago, several attempts have been made at using these organisms as biological control agents against parasitic nematodes causing diseases in plants and animals. The nematophagous fungi capable of destroying free living nematodes can be divided into two groups, predacious and endoparasitic (G. L. Barron; The nematode-destroying fungi; Topics in Mycobiology No. 1, Canadian Biological Publications Ltd., Canada (1977)). J. Gronvold et al., (1987), *Journal of Helminthology*, 61:65–71 (1987); ibid., 62:271–280 (1988); ibid., 63:115–126 (1989), have shown that the predacious fungus *Arthrobotrys oligospora* is capable of reducing the number of infective larvae ($L_3$) of the bovine trichostrongyles *Cooperia oncophora* and *Ostertegia ostertagi* in dung and herbage. *Arthrobotrys oligospora* is one of the species most investigated in attempts of bio-control (J. Gronvold et al., *Journal of Helminthology*, 69;119–125 (1985); P. Nansen et al., *Veterinary Parasltology*, 26:329–337 (1988)), but it is not necessarily the most efficient one.

All previous attempts have failed because of the lack of nematophagous fungi, Including *Arthrobotrys oligospora*, which are able to pass through the intestinal tract of the animal and subsequently reduce the Infection of the herbage effectively.

M. Peloille, IOBC/WPRS Bulletin XIV/2 (1991) has studied the criteria which should be taken into consideration when selecting effective predacious fungi. These criteria are growth rate at different temperatures, predacious activity, ability to survive passage through the intestinal tract of animals, end ability to produce chlamydospores which can be used for the dispersal of the fungi. *Duddingtonia flagrans* is mentioned as the species which fulfills all the requirements best. The conclusion which is not based upon scientifically correct experiments is very misleading, because only few of the Duddingtonia fungi actually survive the passage through the Intestinal tract of ruminants.

One reason that the experiments are not scientifically correct is that it is not documented that the experimental and the control animals were comparable with respect to the number of parasite eggs. Furthermore, the animals have only been fed once with a very large dose of the predatory fungus (500 g), end even though this passes through the intestinal tract of the animals within 48 hours, the predatory fungus is claimed to be effective for up to 96 hours. Furthermore, there is no reference sample taken at the beginning of the experiment, since the results simply begin after 24 hours. It is. also Important to mention that the author bases her conclusion solely on pure laboratory experiments. It is not documented that the effect of the fungus Is maintained in field experiments.

These defects ere remedied by the selection technique according to the invention, which will be described more fully below.

SUMMARY OF THE INVENTION

An object of the present invention is therefore to provide a method enabling isolation of predacious fungi which have the unusual ability to grow in the dung of the calves after having passed the intestinal tract of the animals. In other words, it has now become possible to feed calves with predacious fungi, which results in a substantial reduction in the content of infective larvae in the cow pats and the subsequent spreading of infective larvae to the surrounding herbage.

Surprisingly it has thus been found that it is possible to select and isolate specific predacious fungi which are effective biological control agents when administered to cattle, sheep, goats, pigs and horses. The present fungi are capable of surviving in the faeces of the animals to an extent such that the number of parasites is reduced by at least 50%. Two of the most preferred fungi which can be selected and isolated by the method of the invention, are both strains of the species *Duddingtonia flagrans*, and they have been found capable of reducing the infection level of the infective larvae spread from cow pats to the grass by approximately 70–90%.

Accordingly, the invention concerns a process for the selection and isolation of nematophagous fungi for use in biological control wherein compost and soil samples are subjected to a three-step selection procedure and subsequently spread on tetracycline chloride/water agar (TCC-WA) plates. The three-step selection procedure consists of 1) a primary stress selection step in vitro wherein the samples are exposed to diluted rumen fluid at 39° C. for 24 hours, and a further selection step in vitro wherein the fungi surviving the primary stress selection step are tested in pure culture by exposure to a range of fluids resembling those of the alimentary tract of domestic animals, and 2) a secondary stress selection step in vivo wherein the fungi are selected on the basis of their ability to pass through the living animals, whereafter the most stress-tolerant isolates are tested for their predacious capacity in a cow dung pat bioassay, and finally 3) the stress selected fungi are optionally tested in a field experiment.

The most preferred fungi which can be selected and isolated in this manner belong to the genus Duddingtonia and are preferably of the species D. flagrans.

Two of the fungal strains selected and isolated by the process of the invention, *Duddingtonia flagrans* CI 3 and *Duddingtonia flagrans* CIII 4, were deposited on Sep. 6, 1991 at DSM—Deutsche Sammlung yon Mikroorganismen und Zellkulturen GmbH (German Collection of Microorganisms and Cell Cultures) under the respective numbers DSM 6703 and DSM 6704.

The present predacious fungi may be administered to the animals in the form of a fungus-containing feed, a fungus-containing feed additive or a lick stone to which the fungi have been applied. A supply device in the form of a release bolus can also be inserted into the animal, from which the fungus material is released slowly in the alimentary tract.

The effect of the administered fungi is measured in a field experiment as illustrated in FIG. 3 which give average numbers of infective *Ostertagia ostertagi* larvae ($L_3$) transmitted to the grass surrounding cow pats from experimental calves. On day 31 and 55 after the deposition of the cow pats, grass in one half circle (0–30 cm from the edge of the cow pats) was harvested and examined for the number of L3-larvae. k: Cow pats from calves that were not fed with nematode-destroying fungus. a, b and c: Cow pats from calved that were fed barley grains with the nematode-destroying fungi (HK II 4)=fungus no. a, (HK II 2 (CIII 4))=fungus no. b and (SK II 2 (CI 3))=fungus no. c, respectively.

Fungus no. b and no. c are strains of *Duddingtonia flagrans*.

The infection of the grass is measured as described in the article "Isolation of Infective Dictyocalus Larvae from Herbage" by R. Jess Jørgensen, Veterinary Parasitology 1, 61–67 (1975).

BRIEF DESCRIPTION OF THE FIGURES

FIG. 3 depicts the effect of the administered fungi in a field experiment. The average number of infective *Ostertagia ostertagi* larvae ($L_3$) transmitted to the grass in one-half circle surrounding the cow pats from the experimental and control calves was measured at days 31 and 55. k denotes the control group (calves fed no fungi); a denotes calves that were fed grain with fungi strain no. HK II 4; b denotes calves that were fed grain with fungi strain no. SK II 2 (CI 3); c denotes calves fed with fungi strain no. SK II 2 (CI 3).

DETAILED DESCRIPTION OF THE INVENTION

Figure 1:
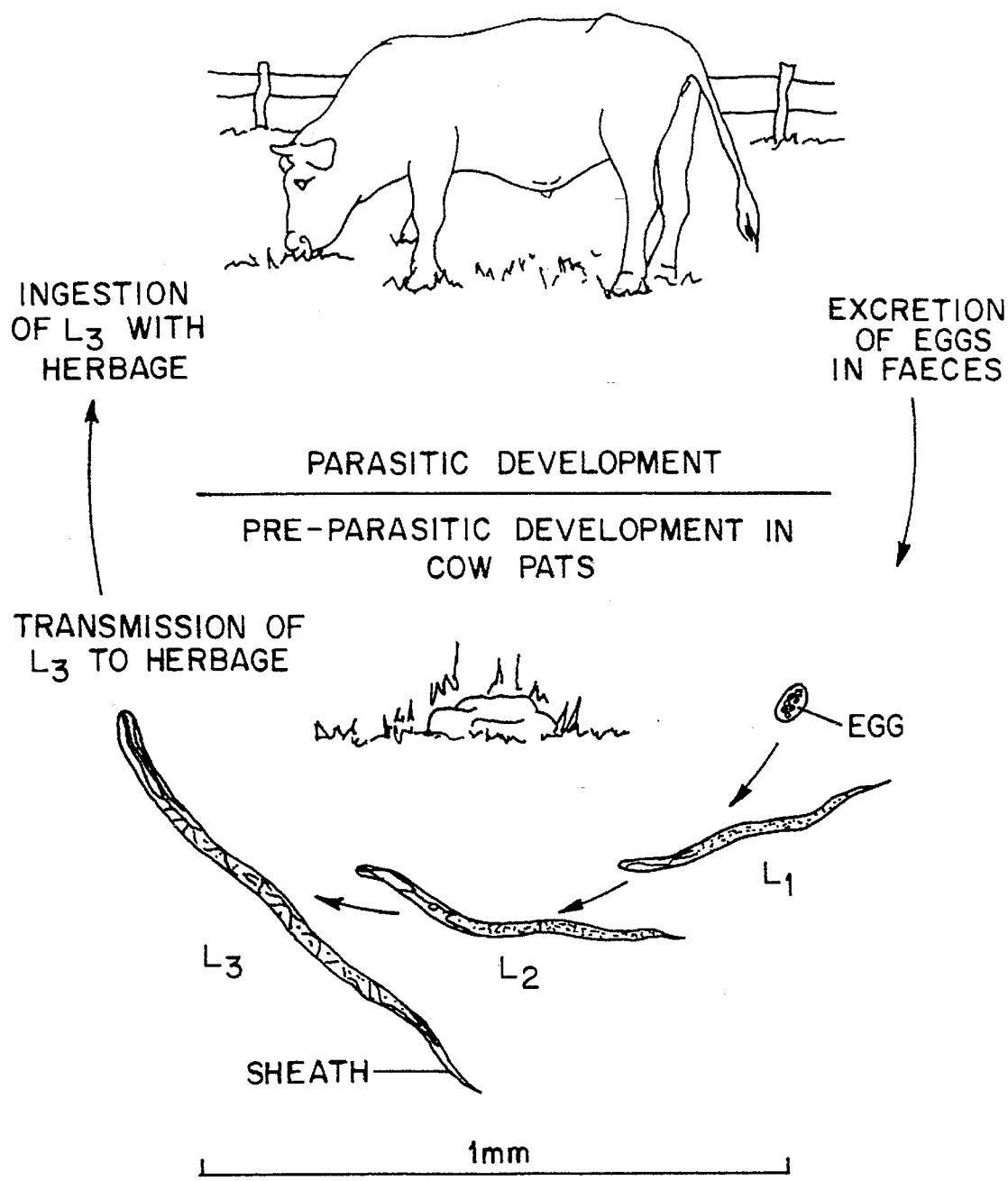
FIG. 1 shows the life cycle of cattle nematode parasites.
Figure 2:
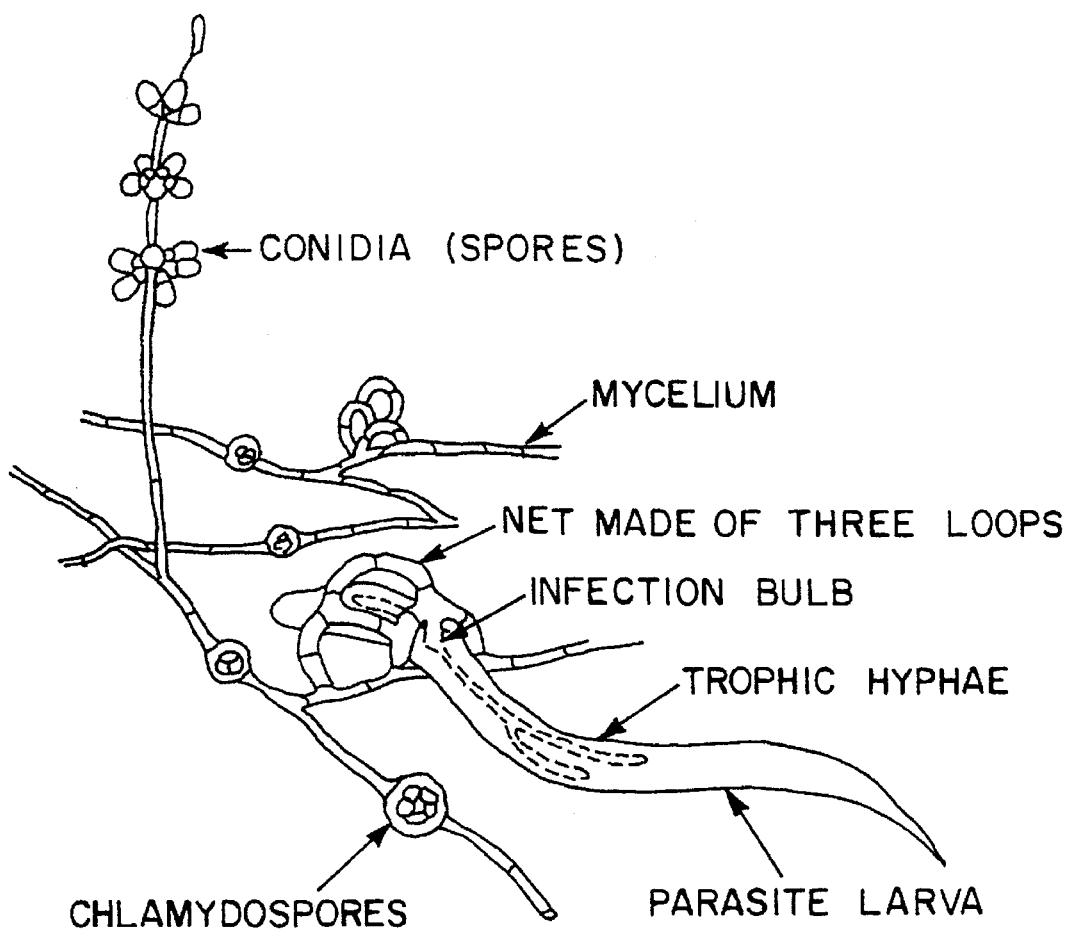
FIG. 2 depicts a nematode larva captured by a predacious fungus.

STRESS SELECTION OF NEMATOPHAGOUS FUNGI
1. In vitro selection of nematophagous fungi for biocontrol of parasitic nematodes in ruminants
Experimental procedure (A) The demonstration of nematophagous fungi in soil and compost samples were made by spreading samples on tetracycline chloride/water agar plates after treatment in sodium hexametaphosphate.

(B) The soil and compost samples were exposed to diluted rumen fluid at 39° C. for 24 h. This will be referred to as the primary stress selection step. The addition of buffer (synthetic saliva) to the rumen fluid ensured that pH was kept within the range normally observed in the rumen. It has been shown that the situation within test tubes resembles the conditions of the rumen when the incubation period was short (J. M. A. Tilley & R. A. Terry, J. Brit. Grassland Society 18, 104–111 (1963); T. Hvelplund & J. Wolstrup, Den Kgl. Veterinær- og Landbohøjskole's Årsskrift 1974, p. 101–107 (The Royal Danish Veterinary and Agricultural University Annual)).

(C) The nematophagous fungi, surviving the above primary stress selection step, were further tested in pure culture by exposure to a range of fluids, resembling those of the alimentary tract of cattle.

(D) The most stress-tolerant isolates were tested for their predacious capacity in a cow dung pat bioassay. The bioassay elucidated both the capacity of the isolated fungi to establish in cattle dung and the efficiency of the fungi to capture nematodes in this environment.

A. Demonstration of nematophagous fungi in soil and compost samples

Sources of fungi

Samples of organic farm soil and compost were taken because they usually have a high content of nematophagous fungi (DACKMAN et al., Microbiol. Ecology 3, 89–93 (1987)). Sampling locations are indicated in Table I.

Media for isolation and cultivation of nematophagous fungi

Tetracycline chloride/water agar (TCC-WA) in petri dishes with a diameter of 8 cm were used for the isolation of fungi from soil and compost. TCC-WA was prepared by mixing sterile filtrated tetracycline chloride with autoclaved water agar (20 g Difco agar in 1 liter demineralized water) at 45°–50° C. The concentration of tetracycline chloride in the final media was 0.02% (w/v). The antibiotic was added to suppress bacterial growth which has previously been shown to make reading of plates difficult. Subsequent isolations and continuous subcultivation of the fungi were performed using 1:10 corn meal agar (CMA, Difco) plates (B. Nordbring-Hertz, Physiologica Plantarum 23, 443–451 (1972)).

Nematodes

*Ostertagia ostertagi* were obtained from the faeces of calves, experimentally infected with a monoculture of this species. After incubation of a faecal culture for 3 weeks at room temperature, third stage larvae ($L_3$) were harvested by a modified Baermann technique. The free-living nematode *Panagrellus redivivus* was cultured axenically in a soy peptone-liver extract medium (B. Nordbring-Hertz, supra). Before use, the larvae of both species were repeatedly washed and resuspended in sterile water.

TABLE I

| | Soil and compost samples used in primary stress selection in diluted rumen fluid |
|---|---|
| CI | Compost soil containing household organic waste from an ecologically managed farm. "Svanholm". |
| CII | Compost from a large scale plant. "Dankompost" Sengel+e,sez o+ee se (household, agricultural and industrial organic waste). |
| CIII | Compost from a large scale plant in H+e,sez o+ee ng (mixed household and garden organic waste). |
| CIV | Compost from private garden containing mainly garden waste. |

TABLE I-continued

| | Soil and compost samples used in primary stress selection in diluted rumen fluid |
|---|---|
| AI | "Svanholm" agricultural soil used for vegetable crops. |
| AII | "Askov" agricultural soil. Only fertilizer used since 1893 has been pig manure. |

Isolation of nematophagous fungi

Samples each of 10 g soil were suspended in 15 ml 0.01% sodium hexametaphosphate in a 100 ml Erlenmeyer flask for 10 min at room temperature. During this period, the flasks were shaken thoroughly. After 5 min rest, 5 replicates of these supernatants (0.5 ml/plate) were spread on TCC-WA plates in a star pattern. Two days later approximately 1000–2000 larvae of *O. ostertagi* and *P. redivivus*, respectively, were added to each of the plates and incubated at room temperature. During the incubation period, nematodes were added to the plates to secure the presence of living nematodes stimulating the activity of the nematophagous fungi. The plates were inspected under a stereo microscope 2–3 times a week for 2 months for growth of nematophagous fungi.

Identification of fungi

The identification of nematophagous fungi was based on the morphology of trapping structures and conidia (R. C. Cooke & B. E. S. Godfrey, Transactions of the British Mycological Society 47, 61–74 (1964); K. Haard, Mycologia 60, 1140–1159 (1968); N. Jarowaja, Acta Mycologica 6, 337–406 (1970) S. Schenck et al., Can. J. Botany 55, 977–985 (1977); K. H. Domsch et al. in Compendium of Soil Fungi vol. 1, 59–64, Academic Press (1980); C.A.N. van Oorschot, Studies in Mycology 26, 61–96 (1985)).

B. Primary stress selection

Test solutions

A buffer solution resembling synthetic saliva was made according to E. I. McDougall, Biochem. J. 43, 99–109 (1948). It was saturated with $CO_2$ at 39° C. and kept at 39° C. until use. Ruminal fluid was collected from a Jersey cow with a ruminal fistula. The fluid was sieved through a sieve (mesh size 1 mm) into a 1 liter container and kept at 39° C. The rumen fluid was diluted 1:4 (v/v) with preheated (39° C.) buffer solution (synthetic saliva).

Primary stress selection procedure

For each of the tested soil samples 75 g was added to 225 ml of diluted rumen fluid in a 300 ml Erlenmeyer flask. The flasks were sealed with airtight rubber stoppers, each supplied with an outlet valve for release of gas, and incubated at 39° C. in a shaking waterbath. After incubation for 24 h the flask rested for 15 min, and the supernatants were carefully decanted. Five replicates (0.5 ml/plate) of each of the supernatants were distributed on TCC-WA plates in a star pattern, as described above. The plates were incubated at room temperature.

Stimulation and isolation of nematophagous fungi was carried out as described above (A).

C. Further test of primary stress selected isolates

Test solutions used for in vitro stress selection

Ruminal fluid was collected and stored, as described above, and used without any further dilution. Synthetic saliva was prepared, as already mentioned. A pepsin-hydrochloric acid solution simulating abomasal fluid was made, according to Tilley & Terry (supra), and adjusted to pH 2.5 by adding NaOH.

A 10% trypsin solution (w/v) in demineralized water was prepared, using Difco trypsin 1:250 and adjusted to pH 7.6. This solution was used as an example of one of the enzymatic stress factors that would be acting in the gut.

The solution was heated at 39° C. before use.

All solutions were prepared on the day they were used.

Test procedure for the test of primary stress selected isolates

For each of the primary isolates ten 1:10 CMA petri dishes (diameter 8.5 cm) were inoculated with 5×5 mm agar blocks, cut out from the periphery of a less than 4 weeks old pure culture. Within 5–7 days the fungal mycelium totally covered the petri dishes. After one week the inoculum blocks were removed, and 1 ml preheated (39° C.) test solution for stress selection (described earlier) was added to the plates. Two dishes were used for each solution tested. The mycelium was scraped off the two plates and the resulting mycelium test media solution was pipetted into a 10 ml tube containing 5 ml of the test solution. For the rumen fluid treatment two tubes were established. The tubes were sealed with rubber stoppers, supplied with gas release valves, and incubated in a waterbath at 39° C.

Following 4 h of incubation two samples of 0.5 ml were taken from each of the tubes, containing buffer solution, pepsin-HCl solution and trypsin solution. Five samples of 0.5 ml were taken from one of the two tubes with rumen fluid after 24 h of incubation. The material in the second tube with rumen fluid was centrifuged (2500 rpm, 10 min) and the supernatant discarded. 5 ml of pepsin-HCl solution was added to the sediment and, after thorough mixing and adjustment to a pH of approximately 2.5 by adding HCl, the material was further incubated for 4 h in the waterbath. At the end of this period two samples were collected and spread on TCC-WA plates. The plates were incubated at room temperature and the stimulation and isolation of the nematophagous fungi was performed, as previously described.

D. Cow dung pat bioassay

Tested fungi

Twelve isolates that survived 24 h treatment in rumen fluid and also 4 h treatment in pepsin-HCl, synthetic saliva and trypsin solutions, were selected for this test. Two isolates that did not survive the 24 h treatment in rumen fluid (CI 1a and AII 1) were included as negative controls.

Cultivation of fungi for bioassay

After treatment with 10% $H_2O_2$ for 30 min in a 300 ml Erlenmeyer flask and washing 3 times in sterile water, 100 g barley grains were mixed 1:1 (w:v) with water and auto-claved. The flasks were inoculated with 3–5 blocks (5×5 mm) from a less than two weeks old pure culture of the primary stress selected fungi. The flasks were shaken thoroughly 2 to 3 times per week, and the different fungus-grain mixtures were used after 2 weeks of cultivation at room temperature (20°–22° C.).

Procedures

Feces from calves infected with a monoculture of *O. ostertagi* was diluted with that from parasite free calves to obtain a concentration of 200–400 eggs per gram (EPG), and 125 g was mixed with 40 barley grains with fungal material. The faeces-barley grain mixture was formed into dome shaped dung pats (approx. 3 cm high). For each fungal isolate, 10 of these dung pats were made and placed in plastic boxes (30×21×13 cm) before incubating at 22° C. and 60–80% relative humidity. Following 3 and 4 weeks incubation, respectively, 5 dung pats were Baermannized in order to extract the third stage larvae of *O. ostertagi*. Dung pats containing eggs, but not inoculated with fungal material, were incubated and harvested 5 per treatment at the same time.

The following results were found:

A. Fungi from soil and compost

A total of 55 nematophagous fungal isolates showing a wide variety of types were obtained from the plates with soil and compost samples. Seven species of predacious fungi capturing nematodes by sticky branches, constricting rings or sticky nets plus three species of endoparasitic fungi were isolated (Table II).

TABLE II

Species of nematophagous fungi isolated from compost and soil samples. The type of capture mechanism is indicated for the different species of predacious fungi (a) Predacious fungi:

| Sticky nets | Constricting rings |
|---|---|
| *Duddingtonia flagrans* | *Dactynella sp.* |
| *Arthrobotrys oligospora* | *Monacrosporium sp.* |
| *A. superba* | Sticky branches |
| *A. amerospora* | *Monacrosporium cionopagum* |

(b) Endoparasitic fungi:

*Harposporium anguillulae*
*Drechmeria coniopora*
*Verticillium sp.*

B. Primary stress selection

The initial selection step reduced the diversity of nematophagous fungi.

Twenty one isolates belonging to only four species of predacious fungi, all producing sticky nets, survived the primary stress selection in diluted rumen fluid. These isolates could be divided into two groups. The first group consisted of eight isolates showing abundant production of intercalary chlamydospores (resting spores) and few conidia on short, conidiophores. The chlamydospores were red-brown, thick-walled, either spherical with a rough, knobbed appearance or ellipsoid with a smooth surface. This type of fungi has been identified as belonging to the genus Duddingtonia with only one species *D. flagrans*. The second group (thirteen isolates) consisted of three different Arthrobotrys spp. (*A. oligospora, A. superba, A. amerospora*) producing large amounts of conidia with one or no septa on branched or unbranched, long conidiophores. The Arthrobotrys spp. also produced chlamydospores, but only in very limited numbers and only in older cultures (from one to two months). The morphological appearance of these chlamydospores differs from the type seen in Duddingtonia. The chlamydospores were the smooth type, ellipsoid to circular, either single or a row of three to five intercalary, swollen, thickened cells with usually just one or very few red-brown pigmented cells in the "chain".

C. Further test of primary stress selected isolates

This qualitative test of the isolates by in vitro stress treatments (Table III) resulted in a further reduction in survivial of isolates, primarily caused by the 24 h treatment in the rumen fluid and rumen fluid with additional pepsin-HCl exposure. In the group of isolates belonging to the Arthrobotrys genus, seven out of thirteen, and only one out of eight of the Duddingtonia isolates, did not show any sign of growth after the rumen treatment. Exposure for 4 h in synthetic saliva, pepsin-HCl solution and trypsin solution did not affect the survival and the potential to produce nets in the fungi.

TABLE III

In vitro stress selection. 13 isolates (A) of nematophagous fungi belong to the genus Arthrobotrys while the he last 8 isolates (B) belong to the genus Duddinggonia. The isolate number code refers to the type of sample (Table I above). In the table "+" indicates growth and "−" indicates no growth.

| Treatment*: | | 1 | 2 | 3 | 4 | 5** |
|---|---|---|---|---|---|---|
| Isolate: | | | | | | |
| A: | | | | | | |
| CI | 1a (control) | + | − | − | + | + |
| CI | 1b | + | − | − | + | + |
| CI | 2 | + | + | − | + | + |
| CII | 1 | + | + | − | + | + |
| CII | 2 | + | + | − | + | + |
| CIII | 1a | + | + | − | + | + |
| CIII | 2a | + | + | + | + | + |
| AI | 1 | + | + | − | + | + |
| AII | 1 (control) | + | − | − | + | + |
| AII | 2 | + | − | − | + | + |
| AII | 3 | + | − | − | + | + |
| AII | 4 | + | − | − | + | + |
| AII | 5 | + | − | − | + | + |
| Isolate: | | | | | | |
| B: | | | | | | |
| CI | 3 | + | + | + | + | + |
| CI | 4 | + | + | − | + | + |
| CI | 5 | + | − | + | + | + |
| CIII | 1b | + | + | − | + | + |
| CIII | 2b | + | + | − | + | + |
| CIII | 3 | + | + | + | + | + |
| CIII | 4 | + | + | − | + | + |
| CIII | 5 | + | + | − | + | + |

*1 synthetic saliva, 4 h: 2 rumen fluid, 24 h; 3 rumen fluid + pepsin-HCl solution, 24 + 4 h; 4 pepsin-HCl solution 4 h; 5 trypsin, 4 h.
**trypsin treatment was only performed once.

When the fungi were exposed to the additional effect of simulated abomasal stress as well as the rumen fluid treatment, only two isolates of the genus Arthrobotrys and three of the genus Duddingtonia survived. Out of these five isolates two fungi that did not survive the treatment in rumen fluid for 24 h (treatment 3, table III), unexpectedly survived the combined treatment of rumen fluid and pepsin-HCl solution.

TABLE IV

The reduction (%) in Ostertagia ostertagi 3rd stage larvae after exposure to different isolates of nematophagous fungi in 125 g dung pats. The dung pats were incubated for 3 and 4 weeks at approx. 22° C., 60–80% RH. After extraction by a modified Baermann technique the reduction % was calculated relative to the controls for the same 2 weeks. The isolate number code refers to the type of sample (Table I).

| | | %-Reduction in *O. ostertagi* $L_3$-Larvae | |
|---|---|---|---|
| | | 3rd week | 4th week |
| Isolate | | | |
| A: | | | |
| CI | 1a | 76 | 65 |
| CI | 2 | 67 | 85 |
| CII | 1 | 74 | 64 |
| CIII | 1a | 72 | 86 |
| CIII | 2a | 86 | 85 |
| AI | 1 | 72 | 73 |
| AII | 1 | 74 | 71 |
| B: | | | |
| CI | 3 | 91 | 95 |
| CI | 4 | 96 | 98 |
| CIII | 1b | 86 | 86 |
| CIII | 2b | 88 | 86 |
| CIII | 3 | 70 | 80 |
| CIII | 4 | 95 | 94 |
| CIII | 5 | 91 | 94 |

A: *Arthrobotrys spp.* B: *Duddingtonia flagrans*

D. Cow dung pat bioassay

The addition of fungal material to the dung pats resulted in a reduction of the number of third stage larvae that could be extracted by the Baermann technique (Table IV). The group of Duddingtonia isolates exhibited a very high reduction capacity (approximately 90%). Within this group, only the isolate CIII seemed less efficient. The addition of the Arthrobotrys isolates resulted in a more diverse and generally lower reduction capacity (approximately 75%). By observation of the dung pats during the incubation period using a stereo microscope with reflected light, conidiophores with conidia, sticky nets and the capture of larvae could be seen on the surface of the dung for species of fungi from both genera.

The above results illustrate that the two-step selection technique of the invention, simulating the ruminant digestive system, is a useful method for selecting nematophagous fungi with the potential to survive the stress factors that will be imposed on the organisms during the passage through a ruminant.

Among the nematophagous fungi isolated after stress selection, the Arthrobotrys species were less resistant to stress treatment compared to the Duddingtonia isolates. The exposure to rumen fluid alone or rumen fluid followed by pepsin-hydrochloric acid treatment appeared to be the main restricting factor. The incubation period for the other three stress treatments were 4 h in contrast to the rumen and rumen plus abomasum simulation that were conducted over a 24 or 24+4 h period, respectively. During this prolonged incubation period, the fungi were exposed to high temperature in addition to the activity of the rumen fluid microorganisms. In the present study it was not possible to distinguish between the effect of these individual important stress factors, but the observation that species of Arthrobotrys seem to be very sensitive to the ruminal stress factors, corresponds with the results of a preliminary in vitro study (unpublished). In this experiment *A. oligospora* conidia or hyphae survived for two days when incubated in water, but only for 4 h when exposed to rumen fluid, and for 4 to 8 h when treated with a pepsin HCl solution, all the treatments being conducted at 39° C.

The present results could indicate that the production of large numbers of thick-walled spherical chlamydospores of the "rough" type in the Duddingtonia isolates, was responsible for the better survival compared to the Arthrobotrys spp. exposed to the same stress conditions.

The dung pat bioassay showed that all of the tested fungi had the ability to compete and function in this particular environment. The bioassay also revealed a higher predacious capacity (approx. 90%) in the group of fungi belonging to the genus Duddingtonia compared to the capacity (approx. 75%) found for species of the genus Arthrobotrys.

The differences in survival and predacious capacity between the species belonging to Arthrobotrys and Duddingtonia, clearly indicate the superiority of the latter. Duddingtonia spp. seem to be the choice for future experiments including oral application of the fungi to ruminants throughout an extended period during a grazing season. However, before such a field trial can be performed, it will be necessary to examine the in vivo passage of selected fungi through housed calves.

In vivo passage through calves of nematophagous fungi selected for biocontrol of parasitic nematodes The above results have shown that a range of nematophagous fungal isolates are able to survive various in vitro stress treatments, simulating the passage through the gastrointestinal tract of a ruminant. In the following, the in vivo survival and subsequent nematode-reducing capacity of these fungal isolates is tested.

Experimental procedure

Calves were fed for four days with barley grains on which the nematophagous fungi had been cultivated. The daily dose was 200 g (dwt), of which 100 g was given just before the morning fodder (7 a.m.), and the remaining 100 g just before feeding in the afternoon (3 p.m.). Feces were collected on day four (morning and afternoon) and day five (morning). After the in vivo passage the fungal material in the faeces was tested for viability and predacious capacity in a dung pat bioassay and in a faecal culture system. To test the survival of the fungi immediately after passage, identifiable barley grains were washed out of the collected faeces and incubated on water agar plates, supplemented with antibiotic.

Fungal material

Ten fungal isolates (Table V), proven to survive the above in vitro stress selection, were used in this experiment. The isolates were maintained on corn meal agar (CMA, Difco) in a dilution of 1:10 (B. Nordbring-Hertz, Nematologica 23, 443–451 (1977)).

Cultivation of fungi

Barley grains were treated with 10% $H_2O_2$ for 30 minutes in 400 ml Erlenmeyer flask, and washed three times in sterile water. Portions of 200 g barley grains were mixed 1:1 (w:v) with water and subsequently autoclaved. The flasks were inoculated with three to five blocks (5×5 mm) from a less than two weeks old pure culture of the previously stress selected fungi, grown on 1:10 CMA. The flasks were shaken thoroughly two to three times per week. After two weeks of cultivation at room temperature (20°–22° C.), the fungus-grain mixtures were ready to be administered to experimental calves.

Reisolation of nematophagous fungi

Tetracycline chloride/water agar (TCC-WA) plates (2% Difco agar and 0.02% tetracycline chloride) were used for reisolation of the fungi.

Specimens of identifiable barley grains in faeces, from the experimental calves, fed fungal material, were washed out of 125 g samples of dung by means of a kitchen sieve. Two TCC-WA plates were inoculated with five grains each, and inspected under stereoscopic microscope one week later for reisolation and identification of the nematophagous fungi.

Identification of fungi

The identification of nematophagous fungi was based on the morphology of trapping structures and conidia as mentioned above.

Experimental calves

Ten parasite-free Jersey or Friesian Black Pied bullocks (four to six months old), weighing between 118 and 182 kg, were used for the passage experiment. One calf was used for each of the fungal isolates tested. The experiment was carried out in five sessions, each including two test calves that were fed fungal material. The calves were kept indoor prior to and during the experiment, and fed with grass pellets and hay.

Parasite material

Faeces, containing eggs of Ostertagia ostertagi, was obtained from two calves, infected with a monoculture of a Danish strain of this species. In the period when parasite females produce eggs, fresh faeces, containing eggs, was collected for both the dung pat bioassay and the faecal culture. Feces, without eggs, was obtained from two uninfected bullocks.

Dung pat bioassay

Faeces from experimental calves, containing fungal material, was diluted 1:1 (w/w) with that from calves containing eggs of O. ostertagi. The number of eggs per gram (EPG) in the final mixture was between 200 and 300. This mixture, containing both parasite eggs and fungal material, was shaped into 125 g dung pats (approx. 3 cm high, diameter 8 cm). For each fungal isolate five dung pats were made and incubated at 22° C. and 60–80% relative humidity. After four weeks O. ostertagi third stage larvae were extracted from the dung pats, using a modified Baermann technique. Dung pats, containing the same number of eggs, but not inoculated with fungal material, were incubated as controls, and harvested five per treatment at the same time.

Faecal cultures

Faecal cultures (10 g faeces samples mixed with 4 g vermiculite and 8 ml $H_{2O}$) were made according to S. A. Henriksen & H. Korsholm, Nordisk Veterinærmedicin 35, 429–430 (1983) by using the same faecal material as described for the dung pat bioassay. For each fungal isolate five cultures were produced. Five cultures containing eggs, but without fungal material, served as controls.

The cultures were incubated under the same conditions as the dung pats, and third stage larvae of O. ostertagi were harvested after four weeks.

Statistical analysis

The difference between the number of developed larvae in treated samples, containing fungal material, and control samples was tested by a one-tailed rank sum test (Mann-Whitney test).

The following results were found:

Nine out of ten nematophagous fungi were reisolated from the faeces after passage through the calves (Table V). The reisolated fungi were all positively identified as the fungi previously given to the calves.

The nematode destroying capacity for eight out of ten fungal isolates was between 61 and 93% in the dung pat bioassay, and between 76 to 99% in the faecal cultures for seven out of the ten fungi (Table V). When the dung pats and the faecal cultures were inspected under a stereo microscope, different fungal structures (conidia, trapping organs or chlamydospores) could be observed directly.

There was a good correlation between the results, obtained from the dung pat bioassay, and the faecal culture technique, except the isolate CI 2.

TABLE V

Re-isolation and test of reduction capacity of ten fungal isolates after passage through calves. Re-isolation of fungi, using barley grains washed out of the freshly passed faeces, was performed on water agar plates with added antibiotic. The reduction capacity was tested in 125 g dung pats and 10 g faecal cultures incubated for four weeks. The difference between used to make inventive sample L1 and conventional sample M1. Sample L1 was test samples and the respective control was tested by a one-tailed rank sum test (Mann-Whitney Utest). The reduction percentage was calculated using the mean values of the fungal isolates and respective controls. Labelling of fungal isolates was according to Larsen et al., J. Helminthol. 65, 193–200 (1991).

| Isolate | Re-isolation of fungi +/− | Faecal Cultures | | | | |
|---|---|---|---|---|---|---|
| | | Median | Range | Sign. | Mean | Red. % |
| CIII 2b | + | 277 | (211–1868) | ** | 771 | 92 |
| CI 2 | + | 1634 | (97–3216) | ** | 1463 | 85 |
| Controls | | 8592 | (6920–15118) | | 9630 | |
| CIII 1b | + | 2414 | (1543–2560) | ** | 2259 | 86 |
| CIII 1a | + | 11595 | (6728–18728) | n.s. | 12295 | 26 |
| Controls | | 16161 | (12764–23041) | | 16541 | |
| CIII 3 | + | 3788 | (2103–6595) | * | 4371 | 61 |
| CI 3 | + | 470 | (138–1588) | ** | 742 | 93 |
| Controls | | 8678 | (4719–20516) | | 11040 | |
| CIII 4 | + | 1768 | (693–2352) | ** | 1505 | 85 |
| CI 4 | − | 3000 | (1671–15124) | n.s. | 6675 | 32 |
| Controls | | 10874 | (3019–16959) | | 9809 | |
| CIII 2a | + | 725 | (592–2607) | ** | 1342 | 91 |
| CIII 5 | + | 1710 | (180–2639) | ** | 1525 | 90 |
| Controls | | 14992 | (9208–20493) | | 14919 | |
| CIII 2b | + | 429 | (350–493) | ** | 409 | 76 |
| CI 2 | + | 1603 | (1275–2137) | n.s. | 1610 | 4 |
| Controls | | 1610 | (1507–1921) | | 1682 | |
| CIII 1b | + | 247 | (223–289) | ** | 254 | 85 |
| CIII 1a | + | 1389 | (1107–2275) | n.s. | 1474 | 12 |
| Controls | | 1476 | (1368–2440) | | 1674 | |
| CIII 3 | + | 74 | (39–102) | ** | 77 | 93 |
| CI 3 | + | 43 | (10–71) | ** | 45 | 96 |
| Controls | | 1269 | (182–1800) | | 1083 | |
| CIII 4 | + | 9 | (4–24) | ** | 11 | 99 |
| CI 4 | − | 887 | (304–1443) | n.s. | 938 | 11 |
| Controls | | 1031 | (760–1466) | | 1057 | |
| CIII 2a | + | 30 | (21–51) | ** | 33 | 99 |
| CIII 5 | + | 31 | (28–37) | ** | 28 | 99 |
| Controls | | 3339 | (1757–4280) | | 3174 | |

*p <0.05
**p <0.01
n.s.: non significant difference

In some previous experiments (not published) it was found that the nematophagous fungus A. oligospora (ATCC 24927) did not survive the passage through cattle, goats or pigs, either when the fungus was grown and fed to the animals on chopped maize, or as pure fungal material. The present invention has shown that nine out of ten previously stress selected nematophagous fungi are able to survive passage through ruminating calves. Seven out of the ten fungi exhibit a high predacious capacity against the free-living larvae of O. ostertagi.

3. Field experiment on biological control of the cattle nematode parasite Ostertagia ostertagi by feeding host animals with nematophagous fungi Field experiments as described in the introduction and illustrated in FIG. 3 confirm the ability of stress selected nematophagous fungi to survive passage through ruminating calves. Experiments have shown that two of the tested fungi, both being Duddingtonia flagrans, are able to reduce the level of infective larvae in the grass by about 70–90%. One such experiment was carried out as follows:

Sixteen calves were divided into two groups with approximately the same total body weight and turned out to graze on each of two fields (day 0). Prior to the grazing season each calf was infected orally with 5000 infective larvae ($L_3$) of the gastrointestinal nematode parasite Ostertagia ostertagi. The experimental fields were of the same size with the same parasitological background, and they contained very few parasitic nematode larvae in the grass at the time of turn out.

From day 14 until day 67 one group of calves was fed a culture of the nematode-trapping fungus *Duddingtonia flagrans* (strain SK II 2=CI 3). On average each calf in the treated group was offered 200 g fungal culture per day in a crib. The fungus was cultured on an autoclaved mixture of barley grains and water in the proportion 1:1 (w/v).

Unfortunately it was not raining during the two months feeding period. As parasite $L_3$-larvae are mainly spread to the grass during rainy weather, it was not possible to follow the effect of the fungus by measuring the number of larvae spread to the grass in this period. But it was possible to register the fungus as a living component in faeces excreted by the animals which were offered fungal culture in the dry period.

Following the feeding period it started to rain on day 75 and $L_3$-larvae were then spread to the grass.

However, on the fields where calves were fed fungal culture, the grass infectivity was reduced by 93% on day 82 and by 67% on day 96 compared to the grass infectivity in the field grazed by the untreated group of animals.

Moreover, the treated group of calves started to excrete significantly lower amounts of parasite eggs in their faeces around day 100–110. Compared to the untreated control group the egg excretion was reduced by 76%.

The present invention has solved a major problem in the attempt to implement the use of nematophagous fungi in biological control of parasitic nematodes in grazing ruminants.

We claim:

1. A method for reducing the population of nematode parasites in the faeces of domestic animals susceptible to infection by said nematode parasites, end thereby reducing the population of said parasites in pastures, comprising orally administering to the animals predacious fungi, said fungi being the progeny of fungi having been preselected to survive in the fasces of the animal, by being subjected to a multi-step procedure comprising:
   (i) In vitro exposure to diluted ruminal fluid at 39° C. for a period of 24 hours;
   (ii) in vitro exposure to solutions simulating conditions in the alimentary tract of domestic animals, said solutions comprising or simulating saliva, ruminal fluid, abomasal fluid and a fluid containing an enzyme that acts in the gut and that subjects said fungi to enzymatic stress; and
   (iii) in vivo passage through the alimentary tract of ruminant mammals, said fungi, after said procedure, possessing the ability to reduce the number of parasitic nematodes in a faecal bioassay by at least 50%.

2. The method for reducing the number of nematode parasites in the fasces of domestic animals susceptible to infection by said nematode parasites according to claim 1, wherein the predacious fungi consist of a biologically pure culture of *Duddingtonia flagrans* CI 3 DSM 6703.

3. The method for reducing the number of nematode parasites in the fasces of domestic animals susceptible to infection by said nematode parasites according to claim 1, wherein the predacious fungi consist of a biologically pure culture of *Duddingtonia flagrans* CIII 4 DSM 6704.

4. The method according to claim 1 wherein the predacious fungi are administered in the form of a feed supplement.

5. The method according to claim 1 wherein the predacious fungi are administered in the form of a lick stone or a release bolus.

6. A method for the selection of predacious fungi for use in biological control of parasitic nematodes in domestic animals, wherein said fungi are subjected to a multi-step selection procedure comprising:
   i) exposing predacious fungi, in vitro, to diluted rumen fluid at
   ii) culturing the predacious fungi surviving step (i) to obtain a purified culture of predacious fungi; 39° C. for a period of 24 hours;
   iii) further exposing the purified culture of predacious fungi to test solutions simulating conditions in the alimentary tract of ruminants, in vitro, the test solutions comprising or simulating saliva, ruminal fluid, abomasal fluid and a fluid containing an enzyme that acts in the gut and that subjects said fungi to enzymatic stress;
   iv) passing the predacious fungi surviving both steps i) and iii) through the alimentary tract of living ruminants, and subjecting fungi surviving said passage to a faecal bioassay to assess the predacious capacity of the fungi; and selecting fungi surviving said passage that possess a predacious capacity sufficient to reduce the number of parasitic nematodes in a faecal bioassay by at least 50%.

7. A method according to claim 6, further comprising confirming the predacious capacity of the fungi selected in step iv) in dung pats in a field experiment.

8. A method according to claim 6, wherein the exposure to the test solutions in step iii) comprises contacting the pure culture of fungi with diluted rumen fluid for 24 hours, followed by contacting the culture for four hours in each of the following solutions: synthetic saliva; diluted rumen fluid; pepsin-HCl; and trypsin solution.

9. The method according to claim 6, wherein the selected fungus belongs to the genus Duddingtonia.

10. The method according to claim 9, wherein the selected fungus is *Duddingtonia flagrans*.

11. A method for biological control of infective larvae of parasitic nematodes, comprising administering to an animal predacious fungi, said fungi being the progeny of fungi preselected by the selection procedure of claim 6 to survive in the faeces of the animal and possessing the ability to reduce the number of parasitic nematodes in faeces by at least 50% as measured by a faecal bioassay.

12. The method for biological control of infective larvae of parasitic nematodes according to claim 11 wherein the predacious fungi consist of a biologically pure culture of *Duddingtonia flagrans* CI 3 DSM 6703.

13. The method for biological control of infective larvae of parasitic nematodes according to claim 11 wherein the predacious fungi consist of a biologically pure culture of *Duddingtonia flagrans* CIII 4 DSM 6704.

14. The method according to claim 11, comprising administering the predacious fungi in the form of a fungus-containing feed or a device releasing a composition containing said fungi for consumption by said animal.

15. The method according to claim 11 wherein the predacious fungi are administered to cattle, sheep, goats, pigs or horses.

16. The method according to claim 11 wherein the number of parasitic nematodes in faeces is reduced by more than 60%.

17. The method according to claim 11 wherein the number of parasitic nematodes in faeces is reduced by more than 75%.

18. The method according to claim 14 wherein the device is a lick stone or a release bolus.

19. A feed supplement for domestic animals consisting of predacious fungi, said fungi being the progeny of fungi having been preselected by the selection procedure of claim 6 to survive in the faeces of the animal and to possess the ability to reduce the number of parasitic nematodes in the faeces by at least 50% as measured by a faecal bioassay.

20. The feed supplement for domestic animals according to claim 19 wherein the predacious fungi consist of a biologically pure culture of *Duddingtonia flagrans* CI 3 DSM 6703.

21. The feed supplement for domestic animals according to claim 19 wherein the predacious fungi consist of a biologically pure culture of *Duddingtonia flagrans* CIII 4 DSM 6704.

22. A composition for reducing the population of nematode parasites in the fasces of domestic animals susceptible to nematode parasitic infection end thereby reducing the population of nematodes in pastures comprising predacious fungi, said fungi having the property of surviving a multi-step selection procedure comprising:

(i) in vitro exposure to diluted ruminal fluid at 39° C. for a period of 24 hours; and (ii) in vitro exposure to solutions simulating conditions in the alimentary tract of domestic animals, said solutions comprising or simulating saliva, ruminal fluid, abomasal fluid and a fluid containing an enzyme that acts in the gut and that subjects said fungi to enzymatic stress; and (iii) in vivo passage through the alimentary tract of ruminant mammals to an extent sufficient to reduce the number of parasitic nematodes in the fasces by at least 50% as measured in a faecal bioassay; said composition being adapted to oral administration to said animals.

23. The composition for reducing the number of nematode parasites in the faeces of domestic animals susceptible to nematode parasitic infection according to claim 22, wherein the predacious fungi consist of a biologically pure culture of *Duddingtonia flagrans* CI 3 DSM 6703.

24. The composition for reducing the number of nematode parasites in the faeces of domestic animals susceptible to nematode parasitic infection according to claim 22, wherein the predacious fungi consist of a biologically pure culture of *Duddingtonia flagrans* CIII 4 DSM 6704.

* * * * *

UNITED STATES PATENT AND TRADEMARK OFFICE
CERTIFICATE OF CORRECTION

PATENT NO. : 5,643,568  
DATED : July 1, 1997  
INVENTOR(S) : Jens WOLSTRUP et al.

It is certified that error appears in the above-identified patent and that said Letters Patent is hereby corrected as shown below:

On the title page, item: [76], Inventors, in the address for the second inventor, Jørn GRØNVOLD, please change "Copehagen N." to --Copenhagen N.--.

Signed and Sealed this

Twenty-seventh Day of January, 1998

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,643,568

DATED : Jul. 1, 1997

INVENTOR(S) : Jens WOLSTROP, Jørn GRØNVOLD, Peter NANSEN, Svend Aage HENRIKSEN, Michael LARSEN It is certified that errors appear in the above-identified patent and that said Letters Patent is hereby corrected as shown below:

On the title page: Item [75]

for inventor Svend Aage Henriksen, add --, Denmark-- after "Hvidovre" ; and in the last line of the Inventors, after "Frederiksberg C", please delete "both of".

Item [56]

Under "Other Publications", col. 2, change two instances of "Gronvold" to --Grønvold--.

In col. 1, line 6, change "USA" to --USC--.

Line 7, change "PCT/DK92100269" to --PCT/DK92/00269--.

In col. 2, line 60, change "Including" to --including--.

Line 62, change "Infection" to --infection--.

In col. 3, line 2, change "end" to --and--.

Line 8, change "Intestinal" to --intestinal--.

Line 21, change "Is" to --is--.

In col. 5, in Table I, in CII (second line), change "Sengel+e,sez o+ee se" to --Sengeløse--.

Table I, in CIII (first line), change "H+e,sez o+ee ng" to --Høng--.

In col. 15, line 38, change "fasces" to --faeces--.

Line 53, change "fasces" to --faeces --.

Line 58, change "fasces" to --faeces--.

UNITED STATES PATENT AND TRADEMARK OFFICE

CERTIFICATE OF CORRECTION

PATENT NO : 5,643,568

DATED : Jul. 1, 1997

INVENTOR(S) : Jens WOLSTROP, Jørn GRØNVOLD, Peter NANSEN, Svend Aage HENRIKSEN, Michael LARSEN It is certified that errors appear in the above-identified patent and that said Letters Patent is hereby corrected as shown below:

In col. 17, line 16 (claim 22), change "fasces" to --faeces--.

In col. 18, line 9 (claim 22), change "fasces" to --faeces--.

Signed and Sealed this

Twenty-third Day of May, 2000

*Attest:*

*Attesting Officer*

Q. TODD DICKINSON

*Director of Patents and Trademarks*